United States Patent [19]

Riemenschneider et al.

[11] 4,082,796

[45] Apr. 4, 1978

[54] PROCESS FOR PREPARING CYANOFORMAMIDE

[75] Inventors: Wilhelm Riemenschneider, Frankfurt am Main; Peter Wegener, Konigstein, Taunus, both of Germany

[73] Assignee: Hoechst Aktiengesellschaft, Frankfurt am Main, Germany

[21] Appl. No.: 642,398

[22] Filed: Dec. 19, 1975

[30] Foreign Application Priority Data

Dec. 21, 1974 Germany ............................. 2460779

[51] Int. Cl.² ............................................. C07C 51/44
[52] U.S. Cl. ................................................. 260/545 R
[58] Field of Search ..................................... 260/545 R

[56] References Cited

U.S. PATENT DOCUMENTS

| 2,804,470 | 8/1957 | Welcher | 260/545 R |
| 2,804,471 | 8/1957 | Welcher | 260/545 R |
| 3,637,843 | 1/1972 | Patton | 260/545 R |
| 3,950,416 | 4/1976 | Patton | 260/545 R |

FOREIGN PATENT DOCUMENTS

| 955,453 | 4/1964 | United Kingdom | 260/540 |
| 1,244,947 | 9/1971 | United Kingdom. | |

OTHER PUBLICATIONS

Yokoyama, et al., C.A. 82 (1975), 139436h.

*Primary Examiner*—Joseph Paul Brust
*Attorney, Agent, or Firm*—Curtis, Morris & Safford

[57] ABSTRACT

Cyanoformamide is prepared when cyanogen is contacted with a catalyst solution containing low molecular aliphatic carboxylic acids, from 0.025 to 1.0 mole/1 of copper-(II)-salts and up to 5% by weight of water. Hydrogen cyanide can be used instead of cyanogen, if the catalyst solution contains nitrate ions in addition.

12 Claims, No Drawings

PROCESS FOR PREPARING CYANOFORMAMIDE

The present invention relates to a process for preparing cyanoformamide, based on cyanogen or hydrogen cyanide.

Derivatives of the unstable cyanoformic acid are important for producing glycine and its derivatives which may be obtained by hydrogenation. They are also important as a starting material in the preparation of unsymmetrically substituted oxalic acid derivatives. They are furthermore important as intermediates in organic synthesis, e.g. for synthezising heterocyclic compounds, and as solvents needed for spinning polyacrylonitrile.

In the past the technical synthesis of cyanoformic acid derivatives was carried out by reacting esters of monochloroformic acid with cyanides. Cyanoformamide may be prepared from the esters of cyanoformic acid by known methods.

Another preparation of cyanoformamide by means of adding water to cyanogen in the presence of a phosphorus containing acid has been made known by U.S. Pat. No. 2,804,741. This process is disadvantageous in that it has a low conversion rate which leads to long reaction periods in spite of the use of pressure vessels.

A process for the preparation of cyanoformamide from cyanogen has now been found, which comprises contacting a temperatures of from 0° to 80° C cyanogen with a solution containing carboxylic acids of low molecular weight (especially having from 1 to 4 carbon atoms), as well copper-(II)-salts and minor quantities of water. A water content of less than 5% is preferred.

The reaction proceeds according to the equation

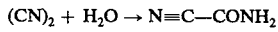

The limit on the water content in the reaction medium is such that the molar ratio water/cyanogen in the reaction mixture is maximum of 1. Although cyanoformamide is also formed at a higher water content such higher water content results in the formation of more and more oxamide by further hydration of cyanoformamide.

A preferred embodiment of this process comprises dropwise addition of water - possibly blended with the above specified carboxylic acids or with other polar solvents - at the same rate as it is reacting with cyanogen in the course of the reaction, so that at any time and at a given location the concentration of water will be as uniform and as low as possible.

If the processing method is a discontinuous one, care has to be taken that after termination of the reaction no more free water is present, otherwise this water will react further during the work-up of the formed cyanoformamide to yield oxamide.

The working temperature ranges from 0° to 80° C, preferably from 30° to 60° C.

Suitable carboxylic acids of low molecular weight may be formic acid, acetic acid, propionic acid and butyric acids. Practical and economic considerations lead to a preference for acetic acid.

It is furthermore possible to add to the reaction solution up to 5 parts by weight of a polar organic solvent for each part by weight of carboxylic acid. These solvents should have water-dissolving properties. Among such solvents are preferred aliphatic ethers and nitriles, especially compounds such as diethyl ether, diisopropyl ether, tetrahydrofurane or glycol ether such as ethylene glycol dimethyl ether and acetonitrile or propionitrile.

Catalysts useful for this reaction include all copper-(II)-salts soluble in the carboxylic acids employed, such as copper-(II)-chloride, copper sulfate, copper acetate, copper chlorate. Preference is given to the use of copper nitrate which is employed generally as $Cu(NO_3)_2 \cdot 3 H_2O$. The copper salts are used in quantities of from 0.025 to 1.0 mole per liter, especially from 0.1 to 0.5 mole/l. Larger quantities are possible, but provide no special advantage.

A particular embodiment of the present invention consists in producing the cyanogen employed as starting material in situ in the same reaction solution in which it is later converted to cyanoformamide. This processing method provides for simultaneously carrying out the formation of cyanogen and the hydration of cyanogen to yield cyanoformamide, both processes being performed in the catalyst solution.

This variation of the process provides for utilizing hydrogen cyanide and oxygen or air, the newly formed intermediary cyanogen not being isolated, but only the cyanoformamide which is formed as final product, being recovered from the reaction mixture, according to the following scheme:

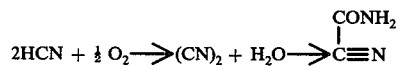

In the foregoing reaction addition of water to the reaction medium can be dispensed with, for one mole of water is formed anyway per mole of cyanogen during the oxidation of hydrogen cyanide. This processing method has the additional advantage of avoiding the formation of a water excess, so that the formation of oxamide by further hydration of cyanoformamide is avoided as well.

The reaction conditions in the catalyst solution remain the same, with the only exception being that the presence of nitrate ions in the catalyst solution is required. It is recommended, therefore, to utilize copper nitrate as a copper salt. However, a different copper salt may be employed as well, provided that in this case a quantity of nitric acid (or rather nitrate ions) approximately equivalent to the copper present has to be added.

In order to maintain the initial pH value of the reaction solution which ranges from $-1$ to $+2$, an occasional supplementary addition of some nitric acid may be required by a continuous processing method.

The reaction is carried out either by introduction of gaseous cyanogen or by pumping liquified cyanogen into the catalyst solution. If cyanogen is produced in situ, hydrocyanic acid in its liquid or gaseous state, and simultaneously, oxygen are introduced into the catalyst solution. The oxygen may be introduced either in its pure state or as a mixture with inert gases, especially as air. If undiluted oxygen is employed, it is advantageous to recycle the exit gas mixture and to make it again contact the reaction solution.

It may also be of interest to provide for recycling of the catalyst solution, so as to improve the cooling effect by additional cooling units. This method provides at the same time a more thorough mixing of the reactants.

The use of hydrogen cyanide may be accompanied by the application of oxygen at stoichiometric quantities, though preference is given to an excess of oxygen of up to 100% or more of the theoretical requirement, especially of from 20 to 50%. Larger excess quantities are possible, but provide no special advantage.

Regardless of whether cyanogen or hydrocyanic acid is utilized as starting material, the reaction may be carried out discontinuously or continuously.

The reaction temperatures may range from 0° to 80° C, advantageously from 30° to 60° C.

The reaction may generally be continued until the catalyst solution contains 30 weight % of cyanoformate. However, to minimize secondary reactions, the reaction may advantageously be interrupted and the reaction solution worked-up upon reaching a 20 weight %, especially a 10 weight % content of cyanoformamide. The quantity of cyanoformamide produced may be calculated as a first approximation from the utilized quantities of the starting products.

The cyanoformamide may be isolated by extraction or by distillation, a possible method being for example a solvent extraction.

When arranging for a work-up by distillation, it is necessary to take into account the fact that cyanoformamide is highly unstable in the presence of copper ions, so that the first work-up step recommended is the elimination of the copper ions. This elimination may take place, e.g. by a precipitation reaction by means of hydrogen cyanide or hydrogen sulfide, the copper precipitating either as copper-(I)-cyanide or as copper-sulfide.

However, the elimination of copper by means of an acid ion exchanger is especially advantageous. The copper may later on be recovered from the ion exchanger according to known methods.

The reaction product is obtained in its pure state by evaporation of the solvent - preferably in vacuo - from the solution freed from copper ions. The remaining cyanoformamide solidifies and has a melting point of 60° C.

A continuous operation provides for a temporary or continuous removal of a partial current of the catalyst solution containing the reaction product. After having recovered the cyanoformamide from this partial current by means of extraction, the remaining catalyst solution is fed back into the reactor. When employing HCN, a water content of the catalyst solution below 3%, especially below 1% is advantageous. This results in suppression of the formation of oxamide which may be produced in trace amounts even at water ratios of about 3 - 5%.

The following examples illustrate the invention:

EXAMPLE 1

A solution of 150 ml of ethylene glycol dimethyl ether, 50 ml of glacial acetic acid and 3 g of $Cu(NO_3)_2 \cdot 3 H_2O$ is prepared in a 250 ml three-necked flask with a $CO_2$-cooling device, thermometer, gas inlet tube, then heated to 40° C. At first there are introduced 25 ml of cyanogen (= 24 g = 0.46 mole) and dissolved. Subsequently in course of 2 hours are added dropwise 10 ml of $H_2O$, while agitating. The temperature rises slightly and the solution becomes somewhat turbid. Subsequently, 8 g of oxamide (= 0.09 mole = 19.5% of the theoretical yield, calculated on cyanogen) may be filtered off. The blue-green tinted filtrate is sent through 100 ml of cations-exchanger (Lewatit S 100) and in this way freed from $Cu^{2+}$-ions. The slightly yellowish tinted discharge is evaporated to dryness at a bath temperature of 45° C in a rotation evaporator. The residue is composed of 25 g of cyanoformamide (melting point: 58° C), i.e. 0.37 mole corresponding to 80% of the theoretical yield, calculated on the cyanogen employed.

EXAMPLE 2

Into a solution of 160 ml of glacial acetic acid and 4 g of $Cu(NO_3)_2 \cdot 3 H_2O$, charged in a 250 ml cylindrical glass flask with gas inlet, is introduced a quantity of 25 ml of gaseous cyanogen at −10° C. After heating to about 35° C, 8 ml of water are dissolved in 40 ml of glacial acetic acid and the mixture added dropwise during one hour, while stirring. The batch is agitated for another half-hour and worked-up as per Example 1. There have been isolated:

| | |
|---|---|
| oxamide: | 10.0 g = 0.11 mole |
| cyanoformamide: | 23.0 g = 0.33 mole |

EXAMPLE 3

A four-necked flask of 1 liter volume is equipped with agitator, gas inlet tube, intensive cooling device and with a thermometer and dropping funnel over an attachment according to Claisen. The gas mixture is recycled into the flask by means of a gas pump. This gas cycle is connected to an oxygen-gasmeter on top of a branch prior to the entrance into the gas pump, so that the total adsorption of oxygen can be measured.

The agitator device is charged with a solution of 12 g of $Cu(NO_3)_2 \cdot 3 H_2O$ in 500 ml of glacial acetic acid, the oxygen cycle is switched on and the vessel is first heated by a bath to 35° C. During a period of from 75 to 90 minutes 50 ml of hydrogen cyanide (= 1.26 mole) are added dropwise from the dropping funnel, a temperature of from 35° to 40° C is maintained by cooling after having started the reaction. The addition being terminated, the agitation is continued for another 10 minutes. The oxygen adsorption amounts to 7.2 l.

From the blue solution, which is immediately cooled, a minor quantity of precipitated oxamide is filtered off. The clear solution is then charged into a column where it flows over 100 ml of Lewatit S 100. The effluent solution is colorless and is concentrated in vacuo in a rotation evaporator (bath temperature 45° C). A residue of 29 g of oil is obtained, which solidifies to crystals of cyanoformamide (melting point: 60° C).

What is claimed is:

1. A process for preparing cyanoformamide which comprises reacting cyanogen with water in a catalyst solution at a temperature of 0° to 80° C. to form cyanoformamide, said solution containing one or more carboxylic acids selected from formic, acetic, propionic and butyric acids, from 0.025 to 1.0 moles per liter of copper(II) salt as a catalyst and water in an amount up to 5% by weight of said solution, adding water to said solution as the reaction proceeds while maintaining the molar ratio of water to cyanogen at a value no greater than 1:1, and recovering the cyanoformamide from said solution.

2. A process according to claim 1 wherein the reaction is carried out at a temperature of 30° to 60° C.

3. A process according to claim 1 wherein the copper(II) salt is a copper nitrate.

4. A process according to claim 1 wherein the cyanogen is produced in situ in the catalyst solution by oxidation of hydrogen cyanide with oxygen in the presence of nitrate ions.

5. A process according to claim 1 wherein the reaction solution contains an aliphatic ether or nitrile in an amount up to 5 parts by weight per part by weight of said carboxylic acid.

6. A process according to claim 1 wherein the cyanoformamide is recovered from the reaction solution by first removing the copper ions therefrom and then distilling the solution in vacuo.

7. A process according to claim 4 wherein the reaction is carried out continuously and gaseous products are recycled and introduced into the reaction solution.

8. A process for preparing cyanoformamide which comprises introducing hydrogen cyanide and oxygen into a reaction medium consisting essentially of one or more carboxylic acids selected from formic, acetic, propionic, and butyric acids and from 0.025 to 1.0 moles per liter of copper(II) salt as a catalyst at a temperature of 0° to 80° C. in the presence of nitrate ions in an amount approximately equivalent to the copper present to form said cyanoformamide and recovering the cyanoformamide from the reaction mixture.

9. A process for preparing cyanoformamide which comprises reacting cyanogen with a catalyst solution at a temperature of 0° to 80° C. to form cyanoformamide, said solution containing one or more carboxylic acids selected from formic, acetic, propionic and butyric acids, from 0.025 to 1.0 moles per liter of a copper(II) salt selected from copper chloride, copper sulfate, copper nitrate and copper chlorate, and water in an amount of up to 5% by weight of said solution and recovering cyanoformamide from said solution.

10. A process for preparing cyanoformamide which comprises reacting cyanogen with a catalyst solution at a temperature of 0° to 80° C. to form cyanoformamide, said solution containing one or more carboxylic acids selected from formic, acetic, propionic and butyric acids, from 0.36 to 5% by weight of water and from 0.025 to 1.0 moles per liter of copper(II) salt soluble in said carboxylic acid as a catalyst, and recovering cyanoformamide from said solution.

11. A process for preparing cyanoformamide which comprises reacting cyanogen with a catalyst solution at a temperature of 0° to 80° C. to form cyanoformamide, said solution containing one or more carboxylic acids selected from formic, acetic, propionic and butyric acids, from 0.025 to 1.0 moles per liter of copper(II) salt soluble in the carboxylic acid, a solvent selected from aliphatic ethers and nitriles in an amount of up to 5 parts by weight per part by weight of carboxylic acid and water in an amount up to 5% by weight of said solution.

12. A process for preparing cyanoformamide which comprises introducing hydrogen cyanide and oxygen into a reaction medium consisting essentially of one or more carboxylic acids selected from formic, acetic, propionic, and butyric acids, an aliphatic ether or nitrile in an amount of up to 5 parts by weight per part by weight of carboxylic acid, water in an amount of up to 5% by weight of said solution and from 0.025 to 1.0 moles of copper(II) nitrate per liter to form said cyanoformamide, and recovering the cyanoformamide from the reaction mixture.

* * * * *